United States Patent [19]

Appleton et al.

[11] Patent Number: 4,803,216
[45] Date of Patent: Feb. 7, 1989

[54] PYRAZOLE-3-AMINES AS ANTI-INFLAMMATORY AGENTS

[75] Inventors: Richard A. Appleton, Wycomb Nr Melton Mowbray; John Dixon, Great Dalby; Sidney C. Burford, Loughborough, all of England

[73] Assignee: Fisons plc, Ipswich, England

[21] Appl. No.: 46,656

[22] Filed: May 5, 1987

[30] Foreign Application Priority Data

May 7, 1986 [GB] United Kingdom ............ 8611102
Dec. 24, 1986 [GB] United Kingdom ............ 8630906

[51] Int. Cl.$^4$ ............ A61K 31/415; C07D 231/38
[52] U.S. Cl. ............ 514/407; 548/375
[58] Field of Search ............ 514/406, 407; 548/375

[56] References Cited

PUBLICATIONS

Chem. Abst., 105 (1986)—42796f.
Chem Abst.-71 (1969)—22058t.

Primary Examiner—Stanley J. Friedman
Attorney, Agent, or Firm—Marshall, O'Toole, Gerstein, Murray & Bicknell

[57] ABSTRACT

There are described compounds of formula I,

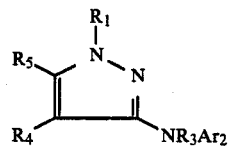

in which $R_1$ represents hydrogen, alkyl, alkanoyl or alkyl substituted by $Ar_1$, $R_3$, $R_4$ and $R_5$, which may be the same or different, each independently represent hydrogen, alkyl or $Ar_3$, $Ar_1$, $Ar_2$ and $Ar_3$, which may be the same or different, independently represent phenyl or phenyl substituted by one or more of alkyl, hydroxy, alkoxy, $NR_6R_7$ or halogen, $R_6$ and $R_7$, which may be the same or different, independently represent hydrogen or alkyl, and pharmaceutically acceptable acid addition salts thereof.

Compositions containing the compounds and methods for their preparation are also described.

The compounds are indicated for use as pharmaceutical, e.g. anti-inflammatory, agents.

10 Claims, No Drawings

PYRAZOLE-3-AMINES AS ANTI-INFLAMMATORY AGENTS

This invention relates to new heterocyclic compounds, processes for their preparation and compositions containing them.

Chemical Abstracts, Vol 71, 1969, 22058Z describes several 3-aryl-5-methylpyrazol-3-amines but does not disclose any pharmaceutical uses of these compounds.

The Indian Journal of Chemistry, Section B, 1985 24(B), 472-6 describes several 3,5-diarylpyrazol-3-amines but does not disclose any pharmaceutical uses of these compounds.

Pyrazole-3-amines are also described in Chemische Berichte, 1962 95 937-43, Chemische Berichte 1969, 100, 2577-2584, and in East German Patent No. 211343.

We have now found that certain pyrazol-3-amines have useful pharmacological properties.

According to the invention there are provided the compounds of formula I,

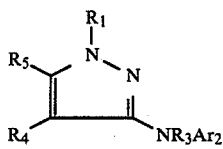

in which $R_1$ represents hydrogen, alkyl, alkanoyl or alkyl substituted by $Ar_1$, $R_3$, $R_4$ and $R_5$, which may be the same or different, each independently represent hydrogen, alkyl or $Ar_3$, $Ar_1$, $Ar_2$ and $Ar_3$, which may be the same or different, independently represent phenyl or phenyl substituted by one or more of alkyl, hydroxy, alkoxy, $NR_6R_7$ or halogen, $R_6$ and $R_7$, which may be the same or different, independently represent hydrogen or alkyl, and pharmaceutically acceptable acid addition salts thereof, for use as a pharmaceutical.

According to the invention there are also provided the novel compounds of formula I, as hereinbefore defined, provided that (i) when $R_1$, $R_3$ and $R_4$ each represent hydrogen, and $R_5$ represents methyl, then $Ar_2$ does not represent phenyl or phenyl substituted by alkyl, alkoxy or halogen and (ii) when $R_1$, $R_3$ and $R_4$ each represent hydrogen and $Ar_2$ represents phenyl or phenyl substituted by alkyl, then $R_5$ does not represent phenyl or phenyl substituted by alkyl, alkoxy or halogen and (iii) when $R_1$ and $R_3$ represent hydrogen, and $Ar_2$ represents phenyl, then (a) $R_4$ and $R_5$ do not both represent phenyl and (b) $R_5$ does not represent hydrogen when $R_4$ represents alkyl, and pharmaceutically acceptable acid addition salts thereof.

According to the invention there is further provided a process for the preparation of compounds of formula I or pharmaceutically acceptable acid addition salts thereof, which comprises (a) reacting a compound of formula II,

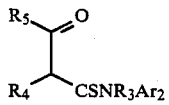

in which $Ar_2$, $R_3$, $R_4$ and $R_5$ are as defined above, with a compound of formula III, $$R_1NHNH_2 \quad \text{III}$$

in which $R_1$ is as defined above, or (b) producing a compound of formula I in which $R_1$ represents alkyl, alkanoyl or alkyl substituted by $Ar_1$, by reacting a corresponding compound of formula I in which $R_1$ represents hydrogen, with a compound of formula IV, $$R_{1a}\text{-}X \quad \text{IV}$$

in which $R_{1a}$ represents alkyl, acyl or alkyl substituted by $Ar_1$ and X represents a good leaving group, (c) aromatising a compound of formula V,

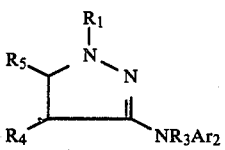

in which $R_1$, $R_3$, $R_4$, $R_5$ and $Ar_2$ are as defined above, (d) producing a compound of formula I in which $R_1$ represents hydrogen, by aromatising a compound of formula VI,

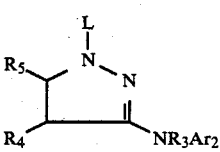

in which L represents a leaving group and $R_3$, $R_4$, $R_5$ and $Ar_2$ are as defined above, or (e) producing a compound of formula I in which one or more of $Ar_1$, $Ar_2$ and $Ar_3$ is substituted by at least one —OH, by removing one or more protecting groups from a corresponding compound of formula VII,

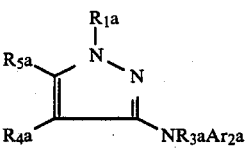

in which $R_{1a}$, $R_{2a}$, $R_{3a}$, $R_{4a}$, $R_{5a}$ and $Ar_{2a}$ are as defined above, save that in addition $R_{1a}$ may represent alkyl substituted by $Ar_{1a}$ and any one of $R_{3a}$, $R_{4a}$ or $R_{5a}$ may represent $Ar_{3a}$, in which at least one of $Ar_{1a}$, $Ar_{2a}$ and $Ar_{3a}$ bears at least one protected hydroxy group, and where desired or necessary converting the resulting compound of formula I into a pharmaceutically acceptable acid addition salt thereof or vice versa.

The cyclisation reaction (a) is preferably carried out in a polar solvent, e.g. ethanol, at a temperature of from about 25° to 75° C.

The process of reaction (b) is preferably carried out in a solvent. The solvent is preferably inert to the reaction conditions, e.g. a polar, aprotic solvent such as 1,4-dioxan, dimethylformamide or N-methylpyrrolidone. The reaction may, if desired, be carried out in the presence of a non-nucleophilic base, e.g. sodium carbonate, sodium hydride or potassium t-butoxide. Good leaving groups that X may represent include tosylate and halide, e.g. chloride, bromide and iodide. The reaction may be carried out at a temperature of from about 0° to 150° C.

The aromatisation of process (c) may be carried out in the presence of an agent which is capable of accepting hydrogen, for example palladium or charcoal. The aromatisation may be carried out by bubbling air or oxygen through a solution of the compound of formula V in an inert solvent, e.g. an halogenated hydrocarbon. However we prefer to carry out the aromatisation using an oxidising agent, e.g. a metal oxide such as manganese dioxide. The oxidation is preferably carried out in a solvent which is inert to the reaction conditions, e.g. in an halogenated hydrocarbon, at a temperature of from about $-70°$ to $150°$ C.

Leaving groups that L may represent in the aromatisation of process (d) include halogen, Oacetyl and especially arylsulphonyl, for example, tosyl. The aromatisation may be effected by heating. However we prefer to carry out the reaction in the presence of a base, e.g. a metal alkoxide in an alcohol. Sodium ethoxide in ethanol is particularly suitable. The reaction may be carried out at a temperature of from 40° to 150° C.

Protected hydroxy groups that $Ar_{1a}$, $Ar_{2a}$ and $Ar_{3a}$ may bear include alkyloxy, e.g. methoxy, acetoxy, trifluoroacetoxy and arylmethoxy, e.g. phenylmethoxy. Other protecting groups are well known and include those described in Protective Groups in Organic Chemistry, ed J. W. F. McOmie, Plenum Press (1973) and Protective Groups in Organic Synthesis, T. W. Greene, Wiley-Interscience (1981). Removal of the protecting group depends on the nature of the protecting group; conventional techniques may generally be employed, including acidic or basic cleavage or hydrogenolysis. For example protecting alkyl or phenylalkyl groups may be removed using a protic acid, e.g. hydrochloric acid or hydrobromic acid at a temperature of from 0° to 150° C., or a Lewis acid, e.g. by reacting with boron trihalide in a halocarbon solvent. When the protecting group is alkanoyl or haloalkanoyl, cleavage may be effected using a base, e.g. sodium hydroxide, in a suitable solvent, e.g. aqueous ethanol. Lewis bases, e.g. pyridine hydrochloride, may be used to cleave alkyl or phenylalkyl groups. Arylmethyl groups, e.g. benzyl, may be removed by catalytic hydrogenation using a suitable catalyst, e.g. palladium, in a suitable solvent, e.g. ethanol or acetic acid. Further methods for the removal of protecting groups are described in both McOmie and Greene, loc. cit. Both McOmie and Greene also describe numerous methods for the application of protecting groups.

Compounds of formula V may be prepared by reacting a compound of formula VIII,

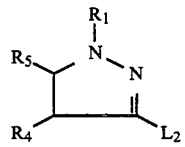

in which $L_2$ represents a leaving group and $R_1$, $R_4$ and $R_5$ are as defined above, with a compound of formula IX,

in which $R_3$ and $Ar_2$ are as defined above.

The reaction may be carried out by heating the two reactants with or without a solvent, e.g. at a temperature of 50° to 250° C. Suitable leaving groups that $L_2$ may represent include halogen, e.g. chlorine, $NH_2$ and hydroxy.

Compounds of formula VI may be prepared from compounds of formula V in which $R_1$ represents hydrogen by conventional techniques, for example when L represents p-toluenesulphonyl, compounds of formula VI may be prepared by reacting a compound of formula V in which $R_1$ is hydrogen with p-toluenesulphonyl chloride in the presence of a base.

Compounds of formula VII may be prepared by processes analogous to those described in process (a), (b), (c) or (d).

Compounds of formulae II, III, IV, VIII and IX are either known, or may be made from known compounds using conventional techniques known per se.

The acid addition salts of the compounds of formula I may be prepared by reaction of the free base with an appropriate acid. The acid addition salts may be converted to the corresponding free base by the action of a stronger base.

The process as described above may produce the compound of formula I or an acid addition salt thereof. It is also within the scope of this invention to treat any derivatives so produced to liberate the free compound of formula I, or to convert one derivative into another.

The compounds of formula I and the intermediates thereto may be isolated from their reaction mixtures using conventional techniques.

Pharmaceutically acceptable acid addition salts include, e.g. salts of mineral acids, such as hydrohalic acids, e.g. hydrochloric acid or hydrobromic acid, or organic acids such as formic, acetic or lactic acids. The acid may be polybasic, for example sulphuric, fumaric or citric acid.

When $R_1$ represents hydrogen, compounds of formula I may exist in a tautomeric form, formula A,

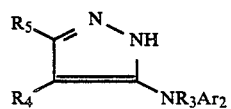

These compounds are included in the scope of the definition of the compounds of formula I.

The compounds of formula I, and pharmaceutically acceptable acid addition salts thereof, are useful because they possess pharmacological activity in animals. In particular, the compounds are useful as broad spectrum anti-inflammatory agents as indicated in one or more of the following assay systems:

(a) Inhibition of lipoxygenases, e.g. 5, 12 and 15 lipoxygenase, in the presence of exogenous arachidonic acid and measurement of the enzyme activity by either a modification of B. A. Jakschik et al, Biochemical and Biophysical Research Communications, 95(1), 103, (1980) using reverse phase HPLC to quantify the products or by a modification of the method of F. F. Sun et al, Prostaglandins 21 (2) 333 (1981) using uv absorption to quantify product formation.

(b) Inhibition of prostaglandin synthetase, utilising bovine seminal vesicle microsomes as the enzyme source after the method of Egan et al Biochemistry 17, 2230 (1978) using either radiolabelled arachidonic acid as substrate and product separation by thin layer chromatography and quantification by scintillation counting or unlabelled arachidonic acid as substrate and a specific radioimmunoassay kit (New England Nuclear) to measure prostaglandin $E_2$ produced.

(c) Inhibition of 5 lipoxygenase activity in intact human neutrophils stimulated by ionophore A23187 and supplemented with exogenous arachidonic acid after the method of P. Borgeat and B. Samuelsson, Proceedings New York Academy of Science 70 2148 (1979) using reverse phase HPLC to measure the products.

(d) Inhibition of formation of arachidonic acid metabolites by mouse peritoneal macrophages challenged in vitro with immune complexes by the method of Blackham et al, J. Pharm. Pharmac. (1985).

(e) Inhibition of $PGE_2$ formation and cell infiltration in the carrageenin sponge model by the method of Higgs et al, Eur. J. Pharmac. 66 81 (1980).

(f) Inhibition of immune complex mediated inflammation in the mouse peritoneal cavity by the method of Blackham et al, J. Pharmac. Methods (1985).

(g) Inhibition of carrageenin oedema in the rat by the method of Winter et al, Proc. Soc. Exp. Biol. 111 544 (1962).

(h) Inhibition of bronchial anaphylaxis in guinea pigs by the method of Anderson, Br. J. Pharmac. 77 301 (1982).

The compounds are indicated for use in the treatment or prophylaxis of inflammatory conditions in mammals, including man. Conditions that may be specifically mentioned are: rheumatoid arthritis, rheumatoid spondylitis, osteoarthritis, gouty arthritis, and other arthritic conditions, inflamed joints;

eczema, psoriasis or other inflammatory skin conditions such as sunburn;

inflammatory eye conditions including conjunctivitis;

lung disorders in which inflammation is involved, e.g. asthma, bronchitis, pigeon fancier's disease and farmer's lung;

conditions of the gastrointestinal tract including aphthous ulcers, gingivitis, Crohn's disease (a condition of the small, and sometimes also of the large intestine), atrophic gastritis and gastritis varialoforme (conditions of the stomach), ulcerative colitis (a condition of the large intestine and sometimes the small intestine) coeliac disease (a condition of the small intestine), regional ileitis (a regional inflammatory condition of the terminal ileum), peptic ulceration (a condition of the stomach and duodenum) and irritable bowel syndrome; pyresis, pain;

and other conditions associated with inflammation, particularly those in which lipoxygenase and cyclooxygenase products are a factor.

For the above mentioned uses the dosage administered will, of course, vary with the compound employed, the mode of administration and the treatment desired. However, in general satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 7.0 mg to 1,400 mg and unit dosage forms suitable for oral administration comprise from 2.0 mg to 1,400 mg of the compound admixed with a solid or liquid pharmaceutical carrier or diluent.

The compounds of formula I, and pharmaceutically acceptable acid addition salts thereof, may be used on their own or in the form of appropriate medicinal preparations for enteral, parenteral or topical administration.

According to our invention we also provide a pharmaceutical composition comprising preferably less than 80% and more preferably less than 50% by weight of a compound of formula I, or a pharmaceutically acceptable acid addition salt thereof, in admixture with a pharmaceutically acceptable adjuvant, diluent or carrier. Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

compositions in a form suitable for administration to the lung include aerosols, particularly pressurised aerosols;

compositions in a form suitable for administration to the skin include creams, e.g. oil-in-water emulsions or water-in-oil emulsion;

compositions in a form suitable for administration to the eye include drops and ointments.

We prefer the composition to contain up to 50% and more preferably up to 25% by weight of the compound of formula I, or of the pharmaceutically acceptable acid addition salt thereof.

The compounds of formula I and pharmaceutically acceptable acid addition salts thereof have the advantage that they are less toxic, more efficacious, are longer acting, have a broader range of activity, are more potent, produce fewer side effects, are more easily absorbed, e.g. orally or have other useful pharmacological properties, than compounds of similar structure.

When $R_1$, $R_3$, $R_4$, $R_5$, $R_6$ or $R_7$ represent alkyl or alkanoyl, the group preferably contains up to 10, more preferably up to six carbon atoms. Particular alkyl groups that $R_1$, $R_3$, $R_4$, $R_5$, $R_6$ and $R_7$ may represent include saturated and unsaturated alkyl groups, for example, methyl, ethyl, 2-propenyl and butyl.

Particular $NR_6R_7$ groups that may substitute the N-phenyl include $-NH_2$, $-NHCH_3$ and $-N(CH_3)_2$.

Particular groups that $R_1$ may represent include hydrogen, acetyl, benzyl, 4-alkoxybenzyl, methyl and isopropyl. We prefer $R_1$ to represent $CH_2Ar_1$, alkyl or hydrogen. We particularly prefer $R_1$ to represent hydrogen when $R_5$ represents $Ar_3$. Specific groups that $Ar_1$ may represent include phenyl and substituted by hydroxy or alkoxy.

We prefer the phenyl group of $Ar_2$ to bear a substituent in the 2- or 4- position. We particularly prefer the phenyl group to bear an OH, alkoxy, e.g. methoxy or dialkylamino group in the 2- or 4- position. An especially favoured group that $Ar_2$ may represent is hydroxyphenyl, in particular 2- or 4-hydroxyphenyl. $Ar_2$ may be further substituted by groups selected from halogen, alkoxy and especially alkyl, e.g. methyl.

We prefer $R_3$ to represent alkyl and particularly hydrogen

We prefer $R_4$ to represent phenyl and particularly hydrogen.

Particular groups that $R_5$ may represent include hydrogen, methyl and $Ar_3$. Particular groups that $Ar_3$ may represent include phenyl and hydroxyphenyl, e.g. 4-hydroxyphenyl.

Certain of the compounds of formula I possess one or more chiral centres and the invention also provides the compounds in the form of their individual optical isomers or as racemic or other mixtures thereof. Certain of the compounds of formula I may also exist as stereoisomers and in these cases the invention provides all stereoisomeric forms. The various isomers may be prepared and/or separated using conventional processes known per se.

The invention will now be illustrated by the following Examples, in which temperatures are in degrees centigrade.

Examples

EXAMPLE 1

N-(4-methoxyphenyl)-3(5)-phenyl-1H-pyrazol-5(3)-amine

Hydrazine hydrate (0.55 ml) was added to a suspension of N-(4-methoxyphenyl)-3-phenyl-thiopropiolamide (2.7 g) in ethanol (20 ml) stirred at room temperature. After 2 hours, the mixture was heated to 60° for 2 hours then cooled to room temperature. The mixture was partitioned between ethyl acetate and dilute aqueous brine. The organic layer was collected and dried. The solvent was evaporated and the residue was recrystallised from ethanol to give the title compound, 1.1 g m.p. 155°–157°.

$C_{16}H_{15}N_3O$: Requires: C=72.45%, H=5.66%, N=15.85%. Found: C=72.36%, H=5.82%, N=15.80%.

EXAMPLE 2

1-Acetyl-N-[4-methoxyphenyl]-1H-pyrazol-3-amine

The compound of Example 1 (1.0 g), acetyl chloride (0.43 g) and pyridine (0.43 g) were stirred together at room temperature for 0.5 hr. The mixture was partitioned between ethyl acetate and aqueous brine. The organic layer was extracted, dried and chromatographed on silica eluting with 5% ethyl acetate/95% dichloromethane, to give the title produced as colourless crystals, 280 mg, mp 123°–124°.

EXAMPLE 3

N-[4-Methoxyphenyl]-1-phenylmethyl-1H-pyrazol-3-amine (a)
4,5-Dihydro-N-(4-methoxyphenyl)-1-phenylmethyl-1H-pyrazol-3-amine 4,5-dihydro-1-phenylmethyl-1H-pyrazol-3-amine (24 g) (prepared by the method of H. Dorm, A. Otto, Chem Ber. 103 2505 (1970), p-anisidine (17.5 g) and p-toluenesulphonic acid (100 mg) was heated at 170° under dry nitrogen until evolution of ammonia ceased. The reaction mix was cooled, purified by chromatography on $SiO_2$ eluting with ether:pentane 1:1 to give the sub-title compound as colourless cubes (13.3 g).

(b)
N-(4-Methoxyphenyl)-1-phenylmethyl-1H-pyrazole-3-amine

To a stirred solution of the product of step (a) (13.3 g) in dichloromethane (250 ml) was added active manganese dioxide in portions until all traces of starting material had disappeared. The reaction mix was filtered, evaporated to a gum and purified by chromatography on silica, eluting with ether, to give the product, mp 68°–71°.

EXAMPLE 4

4-(1-Phenylmethyl-1H-pyrazol-3-yl)aminophenol

The title pyrazole of Example 3 (6.3 g) was heated on a steam bath in a mixture of aqueous HBr (48%, 200 ml) and glacial acetic acid (25 ml) for 6 hours. The reaction mixture was cooled, poured into water, neutralised with sodium bicarbonate, extracted with ethyl acetate, washed with brine, dried and evaporated to give after chromatography the title compound, 1.0 g, mp 114°–116° (from cyclohexane/ethyl acetate).

EXAMPLE 5

2-(1H-Pyrazol-3-yl)aminophenol (a)
4,5-Dihydro-N-(2-methoxyphenyl)-1-(4-toluenesulphonyl)-1H-pyrazol-3-amine A mixture of 4,5-dihydro-1-(4-toluenesulphonyl)-1H-pyrazol-3-amine (8.08 g) (Organic Synthesis 48,8, (1968)), o-anisidine (8.0 g) and glacial acetic acid (80 ml) was heated on a steam bath for 4 hours. The reaction mixture was cooled, filtered and washed with ether to give the sub-title product, 7.6 g, mp 176°–9°.

(b) N-(2-Methoxyphenyl)-1H-pyrazol-3-amine

The product of step (a) (7.5 g) was added to a solution of sodium ethoxide (60 ml, prepared from 0.6 g sodium), at a temperature of 60°. The mixture was refluxed for 10 minutes, cooled, added to water, extracted with ethyl acetate, dried and evaporated to give the sub-title compound as a purple oil, ms 189 ($M^+$).

(c) 2-(1H-Pyrazol-3-yl)aminophenol

The product of step (b) (4.6 g) was dissolved in 48% aqueous HBr (100 ml) and refluxed for 8 hours. The mixture was poured onto water (750 ml), neutralised with solid sodium bicarbonate, extracted with ethyl acetate, washed with brine and evaporated to give the title compound as a white crystalline solid, 0.49 g, mp 163°–4° (from ethyl acetate/cyclohexane).

EXAMPLE 6

2-(1-Methyl-1H-pyrazol-3-yl)aminophenol (a)
N-(2-Methoxyphenyl)-1-methyl-1H-pyrazol-3-amine The pyrazole from Example 5 (b) (4.0 g) was added to a mixture of crushed potassium hydroxide pellets (4.7 g) in dry dimethylsulphoxide, which had previously been stirred for 5 minutes under nitrogen at room temperature. After stirring for 0.75 hours, methyl iodide (3.1 g) was added to the red solution and stirring was maintained for a further 0.75 hours. The reaction mix was poured into water, extracted with ethyl acetate, the organic layer washed, dried, evaporated and chromatographed to give a light brown oil.

(b) 2-(1-Methyl-1H-pyrazol-3-yl)aminophenol hydrochloride

The pyrazole from step (a) (1.7 g) was dissolved in dichloromethane (30 ml) under an atmosphere of nitrogen. Brown tribromide (8 ml) in dichloromethane was added dropwise and the mixture stirred at room temperature for 24 hours. After addition of dilute sodium bicarbonate, the organic phase was removed, dried and evaporated to give a pale oil, which was converted to the hydrochloride salt of the title compound, by trituration with ethereal HCl, to give an off-white solid, 0.75 g, mp 162°–164°.

EXAMPLE 7

4-(5-Phenyl-1H-pyrazol-3-yl)aminophenol

The title pyrazole from Example 1 (3 g) was heated in a mixture of aqueous HBr (30%, 10 ml) and glacial acetic acid (2 ml) on a steam bath for 72 hours. The mixture was cooled, filtered and neutralised with dilute sodium bicarbonate to give the title compound as a colourless solid, 2.2 g, mp 215°–17° (from ethanol).

EXAMPLE 8

The following compounds were prepared by methods analogous to those described in Examples 1 to 7 above:

(a) N-[4-Methoxyphenyl]-1-[1-methyl]ethyl-1H-pyrazol-3amine, oil;
(b) N-[4-Methoxyphenyl]-1-methyl-1H-pyrazol-3-amine, mp 64°–66°;
(c) 5-Methyl-N-phenyl-1-phenylmethyl-1H-pyrazol-3-amine, mp 97°–98°;
(d) N-[4-Methoxyphenyl]-1H-pyrazol-3-amine, mp 95°–96°;
(e) 5-Methyl-N-phenyl-1H-pyrazole-3-amine, mp 130°–131°;
(f) N-[4-Methoxyphenyl]-5-methyl-1H-pyrazol-3-amine, mp 132°–133°;
(g) N-[4-Methoxyphenyl]-1-methyl-5-phenyl-1H-pyrazol-3-amine, mp 107°–108°;
(h) N-[4-Methoxyphenyl]-4,5-diphenyl-1H-pyrazol-3-amine, mp 190°–191°.
(i) 4-[3-(4-Methoxyphenylamino)-1H-pyrazol-5-yl]phenol, mp 170°–172°.
(j) N-(4-Hydroxyphenyl)-1H-pyrazol-3-amine, mp 190°–192°.
(k) 4-(1-methylpyrazol-3-yl)aminophenol, mp 183°–185°.
(l) 1-Methyl-N-(4-dimethylaminophenyl)-1H-pyrazol-3-amino, mp 84°–85°.
(m) 4-(1-(4-Methoxyphenyl)methylpyrazol-3-yl)aminophenol, mp 123°–124°.

We claim:

1. A compound having the formula

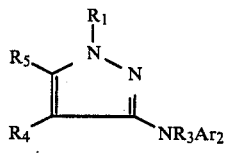

in which $R_1$ represents hydrogen, alkyl, alkanoyl or alkyl substituted by $Ar_1$, $R_3$, $R_4$ and $R_5$, which may be the same or different, each independently represent hydrogen, alkyl or $Ar_3$, $Ar_1$, $Ar_2$ and $Ar_3$, which may be the same or different, independently represent phenyl or phenyl substituted by one or more of alkyl, hydroxy, alkoxy, $NR_6R_7$ or halogen, $R_6$ and $R_7$, which may be the same or different, independently represent hydrogen or alkyl, provided that (i) when $R_1$, $R_3$ and $R_4$ each represent hydrogen, and $R_5$ represents methyl, then $Ar_2$ does not represent phenyl or phenyl substituted by alkyl, alkoxy or halogen and (ii) when $R_1$, $R_3$ and $R_4$ each represent hydrogen and $AR_2$ represents phenyl or phenyl substituted by alkyl, then $R_5$ does not represent phenyl or phenyl substituted by alkyl, alkoxy or halogen, and (iii) when $R_1$ and $R_3$ represent hydrogen, and $Ar_2$ represents pheyl, then, (a) $R_4$ and $R_5$ do not both represent phenyl and (b) $R_5$ does not represent hydrogen when $R_4$ represents alkyl, and pharmaceutically acceptable acid addition salts thereof.

2. A compound according to claim 1, in which $R_1$ represents hydrogen, $CH_2Ar_1$ or alkyl.

3. A compound according to claim 1, in which $Ar_2$ is phenyl substituted by an OH, alkoxy or dialkylamino group.

4. A compound according to claim 1, in which $Ar_2$ represents hydroxyphenyl.

5. A compound according to claim 1, in which $R_5$ represents hydrogen or $Ar_3$.

6. A compound according to claim 1, which is 4-(5-Phenyl-1H-pyrazol-3-yl)aminophenol or a pharmaceutically acceptable acid addition salt thereof.

7. A compound according to claim 1, which is 4-(1-Phenylmethyl-1H-pyrazol-3-yl) aminophenol, 2-(1H-Pyrazol-3-yl)aminophenol, 2-(1-Methyl-1H-pyrazol-3-yl)aminophenol, or a pharmaceutically acceptable acid addition salt of any one thereof.

8. A compound according to claim 1, which is:
N-(4-methoxyphenyl)-3(5)-phenyl-1H-pyrazol-5(3)-amine,
1-Acetyl-N-[4-methoxyphenyl]-1H-pyrazol-3-amine,
N-[4-Methoxyphenyl]-1-phenylmethyl-1H-pyrazol-3-amine,
N-[4-Methoxyphenyl]-1-[1-methyl]ethyl-1H-pyrazol-3-amine,
N-[4-Methoxyphenyl]-1-methyl-1H-pyrazol-3-amine,
5-Methyl-N-phenyl-1-phenylmethyl-1H-pyrazol-3-amine,
N-[4-Methoxyphenyl]-1H-pyrazol-3-amine,
5-Methyl-N-phenyl-1H-pyrazole-3-amine,
N-[4-Methoxyphenyl]-5-methyl-1H-pyrazol-3-amine, N-[4-Methoxyphenyl]-1-methyl-5-phenyl-1H-pyrazol-3-amine,
N-[4-Methoxyphenyl]-4,5-diphenyl-1H-pyrazol-3-amine,
4-[3-(4-Methoxyphenylamino)-1H-pyrazol-5-yl]phenol,
N-(4-Hydroxyphenyl)-1H-pyrazol-3-amine,
4-(1-Methylpyrazol-3-yl)aminophenol,
1-Methyl-N-(4-dimethylaminophenyl)-1H-pyrazol-3-amino,
4-(1-(4-Methoxyphenyl)methylpyrazol-3-yl)aminophenol, or a pharmaceutically acceptable acid addition salt of any one thereof.

9. A method of treatment of an inflammatory condition, which comprises administration of an effective amount of a compound according to claim 1 to a patient suffering from such a condition.

10. A pharmaceutical composition for treating an inflammatory condition comprising an effective amount of a compound according to claim 1 in association with a pharmaceutically acceptable carrier, diluent, or adjuvant.

* * * * *